United States Patent [19]

Sportoletti et al.

[11] Patent Number: 4,789,681
[45] Date of Patent: Dec. 6, 1988

[54] CYTOPROTECTIVE GUANIDINE DERIVATIVES USEFUL IN ISCHEMIC DISEASES

[75] Inventors: Giancarlo Sportoletti; Pietro Cremonesi; Moniquet Sarret, all of Milan, Italy

[73] Assignee: Italfarmaco S.p.A., Milan, Italy

[21] Appl. No.: 944,949

[22] Filed: Dec. 22, 1986

[30] Foreign Application Priority Data

Dec. 23, 1985 [IT] Italy .................................. 23373/85

[51] Int. Cl.$^4$ .................. A61K 31/415; C07D 233/88
[52] U.S. Cl. .................................. 514/392; 514/397; 514/398; 514/401; 514/402; 514/529; 514/538; 514/551; 548/315; 548/316; 548/337; 548/348; 548/351; 560/35; 560/125; 560/168
[58] Field of Search .............. 560/168, 35, 125; 548/315, 316, 337, 348, 351; 514/352, 538, 397, 551, 398, 529, 401, 402

[56] References Cited

U.S. PATENT DOCUMENTS 4,282,217 8/1981 Baglioni et al. .................... 514/169
4,308,280 12/1981 Sportoletti et al. ................ 514/565

OTHER PUBLICATIONS

Chemical –Abstracts, 95:109,306s (1981), [Ger. Offen. 3,027,039, Baglioni, et al., 7/2/81].

Primary Examiner—Richard A. Schwartz
Attorney, Agent, or Firm—Walter H. Schneider

[57] ABSTRACT

Compounds of the general formula I

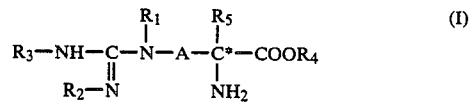

wherein $R_1$ is hydrogen or methyl;

$R_2$ and $R_3$, which are the same or different, represent hydrogen or methyl, or taken together, form the amidine system to which an imidazole or imidazoline ring is bound;

$R_4$ is a linear or branched $C_1$-$C_{10}$ alkyl group; cycloalkyl, aryl, aralkyl or hetaryl group;

$R_5$ is hydrogen or methyl;

A is a propylene chain optionally substituted by one or two methyl groups in one or more of the positions thereof; a chain of formula —HN—CH$_2$—CH$_2$— or of formula —N=CH—CH$_2$—; a 1,4-cyclohexylene group optionally substituted by one or more methyl groups; a 1,4-phenylene group optionally substituted by one or more halogen atoms, alkyl groups or $C_1$-$C_4$ alkoxy group with the proviso that, when $R_4$ is methyl or ethyl and $R_1=R_2=R_3=R_5$ are hydrogen, A is different from an unsubstituted propylene chain, are therapeutically useful as antilischemic, cytoprotective and cardioprotective agents.

10 Claims, No Drawings

CYTOPROTECTIVE GUANIDINE DERIVATIVES USEFUL IN ISCHEMIC DISEASES

The present invention concerns compounds having antiischemic and cardioprotective activity, processes for the preparation thereof and pharmaceutical compositions containing them as the active principle.

Particularly, the invention refers to compounds of the general formula I $$R_3-NH-\underset{\underset{R_2-N}{\|}}{C}-\underset{}{N}-A-\underset{\underset{NH_2}{|}}{C^*}-COOR_4 \qquad (I)$$
$$\phantom{R_3-NH-C-}\overset{R_1}{|}\phantom{-A-}\overset{R_5}{|}$$

wherein $R_1$ is hydrogen or methyl;

$R_2$ and $R_3$, which are the same or different, represent hydrogen or methyl, or taken together, form the amidine system to which an imidazole or imidazoline ring is bound;

$R_4$ is a linear or branched $C_1$-$C_{10}$ alkyl group; cycloalkyl, aryl, aralkyl or hetaryl group;

$R_5$ is hydrogen or methyl;

A is a propylene chain optionally subsituted by one or two methyl groups in one or more of the positions thereof; a chain of formula $-HN-CH_2-CH_2-$ or of formula $-N=CH-CH_2-$; a 1,4-cyclohexylene group optionally substituted by one or more methyl groups; a 1,4-phenylene group optionally substituted by one or more halogen atoms, alkyl groups or $C_1$-$C_4$ alkoxy group with the proviso that, when $R_4$ is methyl or ethyl and $R_1$, $R_2$, $R_3$ and $R_5$ are hydrogen, A is different from an unsubstituted propylene chain.

Compounds according to this invention are the following:

(a) $R_1$ is methyl; $R_2$, $R_3$ and $R_5$ are hydrogen; $R_4$ is a linear or branched $C_1$-$C_{10}$ alkyl group and A is a propylene chain optionally substituted by one or more methyl groups.

(b) $R_1$ and $R_5$ are hydrogen; one of $R_2$ and $R_3$ is hydrogen and the other methyl; $R_4$ is a linear or branched $C_1$-$C_{10}$ alkyl group; and A is a propylene chain optionally substituted by one or more methyl groups.

(c) $R_1$ and $R_5$ are hydrogen or methyl; $R_2$ and $R_3$ are hydrogen or methyl and are the same or different, or taken together with the amidine system form an imidazole or imidazoline ring; $R_4$ is a linear or branched $C_1$-$C_{10}$ alkyl group; and A is is $-NH-CH_2-CH_2-$ or $-N=CH-CH_2-$.

(d) $R_1$, $R_2$, $R_3$ and $R_5$ are hydrogen; $R_4$ is a linear or branched $C_1$-$C_{10}$ alkyl group and A is a 1,4-cyclohexylene residue optionally substituted by one or more methyl groups.

(e) $R_1$, $R_2$, $R_3$ and $R_5$ are hydrogen; $R_4$ is a linear or branched $C_1$-$C_{10}$ alkyl group and A is a 1,4-phenylene residue optionally substituted by one or more halogen atoms, $C_1$-$C_4$ alkyl groups or $C_1$-$C_4$ alkoxy groups.

The compounds wherein $R_4$ is methyl or ethyl, $R_1$, $R_2$, $R_3$ and $R_5$ are hydrogen and A is an unsubstituted propylene chain, are respectively the methyl or ethyl ester of the aminoacid arginine already known before and whose antioedema, antischock and antihyperfibrinolytic activities are described in the italian patent applications, in the applicant's name, Nos. 28416 A/79 and 28417 A/79.

The carbon atom labelled by an asterisk in the previous formula I is an asymmetry centre and it should be therefore understood that the invention concerns both the single enantiomeric R or S forms and the racemic mixtures.

The salts of compounds I with pharmaceutically acceptable organic or inorganic acids are also comprised within the scope of the invention.

Example of said acids are hydrochloric, phosphoric, citric, fumaric, methansulfonic, tartaric acids, etc.

It has now been found that both the new compounds of formula I and the known esters of L- or D-arginine are endowed with a remarkable antiischemic and cardioprotective activity making them particulary suited for the use in human therapy.

An essential aspect of the invention is therefore constitued by pharmaceutical compositions containing as active principles the compounds of the invention or the known esters of L- or D-arginine, a new and surprising pharmacological activity thereof, not derivable from the knowledges up to now acquired, has been found.

It is known that the ischemic pathologies form the main death causes in the industrialized countries populations. The medical-social dimensions appear even more relevant when it is taken into account that a disabling condition usually follows an episode, even not per se deadly. The districts involved are mainly the cardiac and cerebral system.

Among the different pathologies, the myocardial infarct, both of thrombotic or ischemic origin, turns out to be one of the more frequent and deadly. The initial mechanism involved in the infarct situations are different, as well as those making more or less serious the damage of the cardiac tissues. The therapy of the acute phase of the infarct is carried out by the use of a series of drugs, from thrombolytics to calcium-antagonists, from anti-arrhytmics to coronaro-dilators, with the aim to eliminate the primary factor of the tissular hypoxic status (for instance: the thrombus, by thrombolytic therapy) with the restoration of the coronary circulation, or to control the effects of the regenerated perfusion, during which the patient, often, suffers from a serious ventricular fibrillation leading him to death.

For the long term prevention, antiaggregant drugs, anti-coagulants, β-blockers, calcium-antagonists and vaso-dilators are used.

The therapies for cerebral "stroke" use the same kind of drugs, belonging to the more various chemical families.

The compounds object of the present invention open new therapeutic possibilities, exhibiting a marked cardio protective activity against the ischemia and subsequent induced reperfusion, as it has been shown in the experimental rats and a protective action against the damage of the cardiac tissue, demonstrable in the guinea-pig isolated heart, in hypoxia and re-oxygenation.

The cardioprotective effects in the rats is evidenced, with respect to the controls, as:

(a) decrease of the percent death-rate;

(b) decrease of the percent occurrence of ventricular tachycardia;

(c) decrease of the present occurrence of the fibrillations;

(d) decrease of the duration in time of tachycardias and of ventricular fibrillations.

In the guinea-pig, the protection of the cardiac tissue, is evidenced, at the electronic microscope, from the integrity of the lysosomial structures, which, in the control hearts, are completely changed at the membrane level.

The compounds I and the L- or D-arginine methyl or ethyl ester exhibit therefore a cytoprotective like activity never observed up to now, opening new perspectives in the therapy and prevention of cardiac and cerebro-vascular pathologies and in different ischemic forms, included renal ischemia, obliterant arteriopathies etc. For the purpose, the compounds of the invention are formulated in suitable pharmaceutical compositions, which may be administered by the oral or parenteral route, using the techniques and excipients or vehicles conventionally used in the pharmaceutical art. Examples of suited pharmaceutical forms comprise capsules, tablets, syrups, powders or granulates, possible sustained-release forms, solutions, vials or small bottles for intravenous or intramuscular administration. In addition to the compounds of the invention, the pharmaceutical compositions may also contain other active principles having complementar or anyhow useful activity. The posology will depend on the patient's condition, on the kind and seriousness of the pathology and of the considered administration route: it will generally range from 5 to 1000 mg per day in one or more administrations.

The compounds of formula I are prepared according to the invention by reacting a compound of formula II

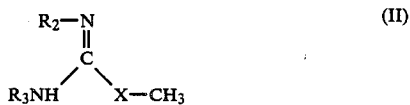

wherein $R_2$ and $R_3$ have the same meanings above defined and X is an oxygen or sulfur atom with a compound of formula III

wherein $R_1$ and $R_5$ have the same meanings above defined, A' has the same meaning as A with the exclusion of the group of formula $-N=CH-CH_2$, and R' is a protecting group of the amino groups.

Alternatively, the compounds I wherein $R_1$, $R_2$ and $R_3$ are hydrogen may be obtained by reacting a compound of formula III with cyanamide $H_2N-CN$ and subsequent hydrolysis. After removal of the possible protective groups, the compounds I are obtained by esterification with alcohols of formula $R_4OH$ or their derivatives, according to known techniques.

The compounds I wherein A is the residue of formula $-N=CH-CH_2$ are prepared by reacting a carbonyl compound of formula IV

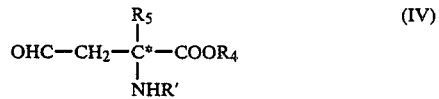

wherein $R_4$, $R_5$ and R' have the same meanings above defined, with a compound of formula V

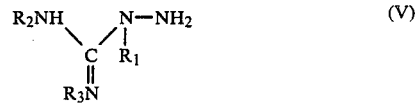

wherein $R_1$, $R_2$ and $R_3$ have the same meanings above defined. Examples of protective groups R' which may be conveniently used comprise the acetyl group, the carbobenzyloxy group or the like.

The esters I are normally obtained in form of hydrochloride, from which the corresponding base may be obtained, for instance by eluition on ion-exchange basic resin or by exchange with wet silver oxide, which may be then salified by neutralization with the desired acid.

The single enantiomers of compounds I may be obtained by optical resolution of the corresponding racemates, through the formation of salts or derivatives with optically active compounds, or by synthesis starting from optically active intermediates III or IV. Whenever during the synthesis other asymmetric centres are introduced, diastereoisomers comprised in the scope of the invention will be obtained. Moreover, when A represents a 1,4-cyclohexylene residue, the cis and trans isomers, with reference to the axial and equatorial bounds of the cyclohexane ring of compound I, may be obtained starting from the corresponding intermediates III having the amino group and the α-amino-carboxymethyl residue respectively cis or trans with reference to the cyclohexane residue. In the following examples, given by way of illustrating and therefore not limiting the invention, the values of the elemental analysis correspond to the theoretical values the NMR data are represented in δ, the IR data in $cm^{-1}$ (recorded in nujol mull ®) and the $\alpha_D$ values in degrees.

EXAMPLE 1

(R)$N^{68}$-methyl-arginine methylester (1a) (R)

21.1 ml of thionyl chloride are slowly added dropwise in 200 ml of anhydrous methanol, cooled to $-10°$ C. The solution is heated at room temperature and 10.5 g of (D)$N^{67}$-methyl arginine (Ann. 1623, 1983) are added thereto. Stirring is continued for 18 hours, and the solvent is then evaporated. The residue is taken up with methanol and evaporated; this step is repeated up to complete disappearance of thionyl chloride.

From the residue, after crystallization from methanol/ethyl ether, 14.9 g of ester are obtained. M.p. 191°–193° C.; $\alpha_D = -22$; I.R.: 3310, 3245, 1745, 1685, 1610, 1595, 1240: NMR (DMSO): 8.80, 8.00, 4.02, 3.75, 3.34, 2.80, 17.25.

(S)$N^\alpha$-methyl-arginine methylester (1a) (S)

It is prepared in the same way as the isomer (R) using (L)$N^\delta$-methyl-arginine, $\alpha_D = +23$.

(R)$N^\epsilon$-methyl-arginine ethylester (1b) (R)

It is prepared in the same way as (1a) using (D)$N^\delta$-methyl-arginine in ethanol.

The product, liquid at room temperature, shows the following signals at the NMR: 8.80, 8.00, 4.30, 4.02, 3.32, 2.80, 1.75, 1.35; $\alpha_D = -23$.

(S)$N^\epsilon$-methyl-arginine ethylester (1b) (S)

It is prepared in the same way as (1a) using (L)$N^{67}$-methyl-arginine in ethanol.

EXAMPLE 2

(R) or (S)N$^G$-methyl-arginine methylester (2a) or n-butylester (2b)

In a similar way to the previous Example, starting from N$^G$-methyl-arginine obtained as described in Anal. Chem. 34, 1414 (1962), the following compounds are obtained.

(R)-N$^G$-methyl-arginine methylester 2a (R); m.p. 201° C.; $\alpha_D = -23$; I.R.: 3310, 3245, 1745, 1685, 1610, 1595, 1240; N.M.R. (DMSO): 8.80, 8.00, 4.02, 3.75, 3.32, 2.80, 1.75;

(S)-N$^G$-methyl-arginine methylester 2a (S) with characteristics identical to (2a R) and with $\alpha_D = +23$;

(R)-N$^G$-methyl-arginine methylester 2b (R) liquid at room temperature; N.M.R.: 8.80, 8.00, 4.30, 4.02, 3.32, 2.80, 1.75, 1.35; $\alpha_D = -23$;

(S)-N$^G$-methyl-arginine ethylester 2b (S); $\alpha_D = +23$, the other characteristics are identical to 2b (R).

EXAMPLE 3

(R) or (S)-γ-methyl-arginine methylester (3a) and ethylester (3b)

By following substantially the process of Example 1, starting from (R) or (S)-y-methyl-arginine (Z. Physiol. Chem. 356, 839, 1975), the following compounds are obtained:

(R)-γ-methyl-arginine methylester 3a (R); m.p. 162°–164° C.; $\alpha_D = -22$; I.R. 3310, 3250, 1745, 1665, 1635, 1605, 1520, 1240; N.M.R. (DMSO): 8.80, 8.05, 7.40, 4.00, 3.75, 3.32, 1.70, 1.05;

(S)-γ-methyl-arginine methylester 3a (S); as in 3a (R) with $\alpha_D = +22$;

(R)-γ-methyl-arginine ethylester 3b (R); liquid at room temperature; $\alpha_D = -21$; I.R. as 3a (R); N.M.R. 8.80, 8.05, 7.40, 4.30, 3.32, 1.70, 1.35, 1.05;

(S)-γ-methyl-arginine ethylester 3b (S); as in 3b (R) with $\alpha_D = +21$.

EXAMPLE 4

(a) (R or S)-2-acetylamino-4-hydrazino-butyrric acid 9.9 g of hydroxylamine-O-sulfonic acid dissolved in 30 ml of water are slowly dripped into a refluxing solution of 44.0 g of (R) or (S)-2-acetylamino-butyrric acid (J. Org. Chem. 14, 813, 1949) and 19.3 g of KOH in 150 ml of water. After further 30 minutes at reflux, acetic acid is added up to pH 6 and the mixture is evaporated under reduced pressure to a volume of about 100 ml. This residue is cooled, filtered, added with benzene (10 ml), warmed a few minutes to 50° C. and finally extracted in ether.

The residue obtained after evaporation of the ether phase is crystallized from H$_2$O/EtOH.

10 g of the title product are obtained.

(b) (R or S)-2-amino-4-guanidyl-aminobutyrric acid 7.9 g S-methyl-isothiouronium iodide were added to 5.73 g of (R or S)-2-acetylamino-4-hydrazinobutyrric acid in 36 ml of 1N NaOH. The mixture is stirred for 4 days at room temperature, the precipitated product is then filtered, dissolved again in HCl 2N and refluxed for 2 hours. After concentration of the solution and filtration of the formed precipitate, 3.2 g of (R or S)-2-amino-4-guanidyl-aminobutyrric acid are obtained.

(c) Methyl (R or S)-2-Amino-4-guanidylamino-butyrrate (4a)

Starting from the compounds obtained in (b), according to the techniques described in the Example 1, the compounds are obtained:

methyl-(R)-2-amino-4-guanidylamino-butyrrate 4a (R); m.p. 178–180; $[\alpha]_D = -22$; I.R. 3315, 3230, 1740, 1670, 1635, 1245; N.M.R. (DMSO): 8.70, 7.30, 4.00, 3.70, 2.90, 1.80.

methyl-(S)-2-amino-4-guanidylamino-butyrrate 4a (S) as 4a (R) with $[\alpha]_D = +22$.

(d) Butyl (R or S)-2-amino-4-guanidylamino-butyrrate (4b)

10.6 ml of acetone dibutylacetal are added to 3 g of (R or S)-2-amino-4-guanidylhydrazino-butyrric acid dissolved in 120 ml of butanol containing 5% HCl. The mixture is kept at 60° C. for 4 hours, then partially evaporated and added with anhydrous ether. An oil is separeted which is dissolved again in butanol with 5% HCl and re-precipitated with ether. The operation is repeated many times (at least three). 1.5 g of purified oil are obtained, having identical characteristics to 4a (R) or (S) except NMR where the signal at 3.70 is absent and signals at 4.30 and 1.30 appear.

EXAMPLE 5

(a) Methyl (R or S)-2-carbobenzyloxyamino-4-oxo-butyrrate 12 g of pyridinium chlorochromate are added to a solution of 10 g of N-carbobenzyloxy-homoserine methylester (Biochemistry 6, 3927, 1967) in 100 ml of anhydrous methylene chloride. After 2 hours stirring at room temperature, further 100 ml of methylene chloride are added and it is filtered on celite. The so obtained solution is evaporated and yields 6.3 of an oil.

(b) Methyl (R or S)-amino-4-oxo-butyrrate 6 g of the compounds obtained in the previous step are dissolved in 100 ml of methanol and subjected to hydrogenolysis in the presence of 600 mg of Pd/C. When the hydrogenation is over, the catalyst is filtered, the solvent is evaporated obtaining 2.8 g of a yellow oil.

(c) Methyl (R or S)-2-amino-4-guanidylimino-butyrrate (5a)

1.7 g of aminoguanidine di-hydrochloride are dissolved in 25 ml of water. A few drops of conc. HCl are then added till the pH is <7. 2 g of methyl (R or S)-2-amino-4-oxo-butyrrate dissolved in 25 ml of methanol, are then slowly dripped into the solution heated to 60° C. The mixture is kept under stirring for 16 hours at the room temperature. The solvent is finally evaporated and the residue recrystallized from methanol. 2.9 g of a product are obtained.

Chemico-physical characteristics:

5a(R): m.p. 161–163; $\alpha_D = -21$; I.R.: 3315, 3215, 1740, 1670, 1630, 1245; N.M.R (DMSO): 8.70, 7.30, 6.50, 4.00, 3.70, 2.90, 1.80.

5a(S): as 5a(R) with $\alpha_D = +21$.

EXAMPLE 6

(a) (R)-2-acetamido-2-(4'-guanidinophenyl)-acetic acid 2.10 g of cyanamide are added to a solution of 2.08 g of N$^\alpha$-acetyl-(4-aminophenyl)-(D)glycine (U.S. Pat. No. 3,464,985) in 10 ml of 1N hydrochloric acid. The reaction is kept at 50° C. for 16 hours, the solvent is then evaporated. The residue, chromatographated on silice, eluent n-propanol/ammonia 7:3, yields 1.8 of a brown oil.

Chemico-physical characteristics:
N.M.R. (D$_2$O): 7.40, 5.20, 1.96.

(b) (R)-2-amino-2-(4'-quanidinophenyl)-acetic acid dihydrochloride 4 g of (R)-2-acetamido-2-(4'-guanidinophenyl-acetic acid are dissolved in 30 ml of 2N hydrochloric acid and refluxed for 2 hours. The solution is dried. 3.5 g of the product are obtained.

Chemico-physical characteristics:
N.M.R. (D$_2$O): 7.40, 5.35.

(c) Methyl (R)-2-amino-2-(4'-guanidinophenyl)acetate dihydrochloride (6a) (R)

The esterification is carried out according to the Example 1.

Chemico-physical characteristics:
Liquid at room temperature; $\alpha_D = -23$; I.R.: 3300, 3250, 1750, 1665, 1635, 1240. N.M.R. (D$_2$O): 7.40, 5.47, 3.85.

(d) N-butyl (R)-2-amino-2-(4'-guanidinophenyl)acetate dihydrochloride (6b) (R)

The esterification is carried out according to the Example 4.

Chemico-physical characteristics:
Liquid at room temperature; $\alpha_D = -22$; I.R.: as 6a (R); N.M.R.: 7.40, 5.47, 4.30, 1.75, 1.30.

(e) Methyl (S)-2-amino-2-(4'-guanidinophenyl)acetate dihydrochloride (6a) (S) e (6b) (S)

They have been prepared in a similar way to the (R) isomer starting from N$^\alpha$-acetyl-(4-aminphenyl)-L-glycine.

Chemico-physical characteristics:
(6a) (R) e (6b) (R) with $\alpha_D = +23$ and $+22$, respectively.

EXAMPLE 7

(a) 2-(R)-acetamido-2-(4'-aminocyclohexyl)-acetic acid 10 g of 2-R-acetamido-2-(4-aminophenyl)-acetic acid dissolved in 65 ml of ethanol are charged into an autoclave. 1 g of 5% Rh/C is added thereto and the mixture is hydrogenated at the temperature of 100° C. and at the initial pressure of 50 atm. The reaction mixture is filtered, washed with the same volume of hot water and evaporated. 10.2 g of a residue comprising the cis and trans isomers are obtained.

The mixture is dissolved in 90 ml of water and treated with 13.5 g of CuCO$_3$.Cu(OH)$_2$ and refluxed for 30 '. The excess copper salts are pump-filtered and ethanol is added to the solution. The obtained precipitate is filtered, washed with ethanol and dissolved in 20 ml of 10% HCl. The obtained solution is treated with hydrogen sulfide till complete precipitation of the copper salt which is separated by centrifugation. The surnatant solution is evaporated, obtaining 2.05 g of (1'-4' cis)-2-(R)-acetamido-2-(4'-aminocyclohexyl) acetic acid.

The solution from which the complex copper salt-cis isomer is separated by ethanol addition is evaporated. The residue is dissolved in 30 ml of 10% HCl and treated with hydrogen sulfide till complete precipitation of the copper sulfide which is separated by centrifugation. The surnatant solution is evaporated. 4.80 g of (1',4' trans)-2-R-acetamido-2-(4'-aminocyclohexyl)-acetic acid are obtained.

Chemico-physical characteristics:
(1',4' cis)-2-(R)-acetamido-2-(4'-aminocyclohexyl)-acetic acid: N.M.R. (D$_2$O): 3.90, 3.20, 2.10, 2.30–1.10;
(1',4' trans)-2-(R)-acetamido-2-(4'-aminocyclohexyl)-acetic acid: N.M.R. (D$_2$O): 3.80, 3.20, 2.10, 2.30–1.30.

(b) (1',4' Cis or trans)-2-(R)-acetamido-2-(4'-guanidinocyclohexyl)-acetic acid hydrochloride 5.77 g of S-methylisothiouronium iodide are added to 4.7 g of (1',4' cis or trans)-2-(R)-acetamido-2-(4'-aminocyclohexyl)-acetic acid dissolved in 27 ml of IN NaOH. The mixture is stirred at room temperature for 4 days. The mixture is then filtered, the precipitate is dissolved in methanol and treated with gaseous hydrochloric acid. 5.1 g of guanidine derivative are obtained.

Chemico-physical characteristics:
(1',4' cis) 2-(R)-acetamido-2-(4'-guanidinocyclohexyl)-acetic acid hydrochloride: N.M.R. (D$_2$O): 4.55, 3.35, 2.10, 2.20–1.25;
(1',4' trans) 2-(R)-acetamido-2-(4'-guanidinocyclohexyl)-acetic acid hydrochloride: N.M.R. (D$_2$O): 4.45; 3.35; 2.10, 2.20–1.20.

(c) (1',4'-cis or trans) 2-(R)-amino-2-(4'-guanidinocyclohexyl)-acetic acid dihydrochloride 5 g of (1',4' cis or trans) 2-(R)-acetamido-2-(4'-guanidinocyclohexyl)-acetic acid hydrochloride dissolved in 50.5 ml of 2N hydrochloric acid are refluxed for 2 hours. The mixture is concentrated and cooled. The obtained precipitate is filtered, yielding 4.6 g of a product.

Chemico-physical characteristics:
(1',4' cis) 2-(R)-amino-2-(4'-guanidinocyclohexyl)-acetic acid dihydrochloride: N.M.R. (D$_2$O): 4.05, 3.35, 2.20–1.20.
(1',4' trans) 2-(R)-amino-2-(4'-guanidinocyclohexyl)-acetic acid dihydrochloride: N.M.R. (D$_2$O): 3.95, 3.35, 2.20–1.20.

(d) Methyl (R) (1',4' cis or trans)-2-amino-2-(4'-guanidinocyclohexyl)-acetate (7a, 7b)

The esterification is carried out according to the Example 2.

Chemico-physical characteristics:
7a(R): m.p.: liquid at room temperature; $\alpha_D = -23$; I.R. 3300, 3250, 1750, 1665, 1240; N.M.R. (D$_2$O): 4.17, 3.85, 3.35, 2.10–1.10.
7b(R): m.p. 36°–37° C.; $\alpha_D = -23$; I.R. at 7a(R); N.M.R. (D$_2$O): 4.07, 3.85, 3.35, 2.20–1.10.

(e) Methyl (S) (1',4' cis or trans)-2-amino-2-(4'-guanidinocyclohexyl)-acetate (7a, 7b)

They are synthesized in a similar way to the (R) isomers starting from 2(S)-acetamido-2-(4-aminophenyl)-acetic acid.

Chemico-physical characteristics:
7a(S): as 7a(R) with $\alpha_D = +23$.
7b(S): as 7b(R) with $\alpha_D = +23$.

EXAMPLE 8

(a)
2-R)-carbobenzyloxyamino-5-(2'-imidazolinylamino)-pentatanoic acid 18 g of N-carbobenzyloxy-(D)-ornithine (Ann. 679, 229, 1964) and 11.8 g of methylthio imidazoline (J. Amer. Chem. Soc. 73, 602, 1951), obtained by treating with NaOH the corresponding hydroiodide, are suspended in 100 ml of a mixture 1:1 MeOH/H$_2$O. The suspension is heated to 65° C. and is stirred for 3 hours absorbing the developing methylmercaptan in sodium hypochlorite. The mixture is allowed to stand overnight and it is then evaporated. The oily residue is shaken several times with acetone till complete removal of excess methylthioimidazoline and then crystallized from MeOH-ethyl ether.

12 g of a product are obtained.
Chemico-physical characteristics:
N.M.R. (D$_2$O): 7.30, 5.00, 3.90, 3.50, 3.00, 1.80–1.20

(b) 2(R)-amino-5-(2'-imidazolinyl-amino)pentanoic acid dihydrochloride

A solution of 8 g of 2(R)-carbobenzyloxyamino-5-(2'-imidazolinyl-amino)-pentanoic acid in 60 ml of ethanol was added with 0.8 g of Pd/C and subjected to hydrogenation at room temperature and pressure. After filtration, the solvent is evaporated. The residue is dissolved in 50 ml of 1N hydrochloric acid and evaporated again. 6 g of the product are obtained.

Chemico-physicol characteristics:
N.M.R. (D$_2$O): 3.60, 3.20, 1.50.

(c) Methyl (R)-2-amino-5-(2'-imidazolinyl-amino)pentanoate (8a) (R)

The esterification is carried out according to the Example 2.

(d) Methyl 2-amino-5-(2'-imidazolinyl-amino-pentanoate (8a) (S)

It is prepared in a similar way to the (R) isomer using $N^\alpha$-carbobenzyloxy-(L)-ornithine.

Chemico-physical characteristics:
8a(R): m.p. 38°–40° C.; $\alpha_D = -22$; I.R.: 3300, 3250, 1750, 1670, 1635, 1235; N.M.R.: 4.30, 3.9, 3.7, 3.4, 2.95–1.6.
8a(S): as for 8a(R) with $\alpha_D = +22$.

EXAMPLE 9

Methyl (R) or (S) (1',4' cis or trans) 2-amino-2-(4'-imida-zolinyl-amino-cyclohexyl)-acetate (9a:cis) (9b:trans)

The derivatives have been synthesized starting from cis or trans 2-aminoacetyl-2-(4'-amino-cyclohexyl) acetic acids prepared according to the Example 7 by reaction with methylthio imidazoline.

Chemico-physical characteristics:
9a(R) m.p.: liquid at room temperature; $\alpha_D = -23$; I.R.: 3300, 2250, 1745, 1660, 1635, 1240; N.M.R. (D$_2$O): 4.17, 3.90, 3.85, 3.35, 2.10–1.10.
9b(R): m.p. liquid at room temperature; $\alpha_D$ e I.R. as 9a(R); N.M.R. (D$_2$O): 4.07, 3.90, 3.85, 3.35, 2.20–1.00

EXAMPLE 10

Methyl (R) or (S) 2-amino-2-(4'-imidazolinyl-amino-phenilacetate (10a)

The derivatives are prepared starting from the (R or S)-2-aminoacetyl-2-(4'-aminophenyl) acetic acid described in Example 6, using 2-methylthio-imidazoline.

Chemico-physical characteristics:
10a(R): m.p. 57°–59° C.: $\alpha_D = -22$. I.R.: 3300, 3250, 1750, 1660, 1630, 1240; N.M.R. (D$_2$O): 7.40, 5.47, 3.90, 3.85.
10a(S): as for 10a(R) with $\alpha_D = +22$.

BIOLOGICAL ACTIVITIES

The derivatives object of the present invention have been subjected to some biological tests and to the evaluation of acute toxicity in mice. The LD$_{50}$ values turned out to be higher than 1000 mg/kg, by the oral route, and of about 500 mg/kg for i.v.

IN VITRO ACTIVITY IN THE GUINEA-PIG ISOLATED HEART

In the isolated guinea-pig heart test according to Langerdoff the derivatives did not show any activity, whereas in the same test wherein the perfusion liquid was deprived of oxygen (hypoxic heart, situation equivalent to the ischemia in vivo) the derivatives exhibited a protective activity against tachyarrthmias and fibrillations induced by said situation. The histological examination carried out at the electronic microscope showed the impairment of the subcellular structure destruction. On the same isolated heart test, the derivatives showed also a protective activity agains fibrillations detected when, after the hypoxic condition, the initial oxygenation condition was restored (situation equivalent to the "in-vivo" reperfusion). The analysis of the lysosomial enzymes released in the perfusion liquid, both at the hypoxic state and during reoxygenation, showed an antagonizing effect of the enzymatic release of the compounds according to the present invention.

The active doses were ranging from 1 to 10 mM (in the perfusion liquid).

IN VIVO ACTIVITY IN THE RAT (CARDIAC ISCHEMIA)

It has been used a cardiac ischemia and reperfusion model, on the anaesthetized rat, by ligation of the left coronary artery as described by C. Clark (C. Clark—J. Pharmacol. Methods, V. 3, 357, 1980). In said model, after the ischemic state induced by the coronary ligation, the reperfusion of the cardiac tissue follows the release of the ligation itself. In said situation tachycardias, extrasystoles ventricular fibrillations are observed, followed, in most cases,.by the animal's death.

The compounds of the invention showed (by i.v. administration from 10' to 30' before ligation or orally 1 hour before), as reported in the following Table 1, an ability of protecting the animal both with reference to the electric impairments and to death-rate. This applies in both situation: hypoxia and reperfusion.

TABLE I

| Product admin. route/ dose in mg/kg | % EFFECTS (with respect to controls in the same situation) ON: | | |
|---|---|---|---|
| | TACHY-CARDIA V. | FIBRIL-LATIONS | DEATH-RATE |
| Saline (controls)/i.v. | (100% of animals) | (90% of animals) | (80% of animals) |

TABLE I-continued

| Product admin. route/ dose in mg/kg | % EFFECTS (with respect to controls in the same situation) ON: | | |
|---|---|---|---|
| | TACHY-CARDIA V. | FIBRIL-LATIONS | DEATH-RATE |
| 0,1 ml/100 g p.c. | | | |
| L.A.M.(*)/iv/3 | 90 | 60 | 20 |
| L.A.M./os/30 | 70 | 55 | 35 |
| D.A.M.(⁁)/iv/i | 60 | 45 | 10 |
| D.A.M./os/10 | 60 | 35 | 0 |
| L.A.E.(°)/iv/3 | 60 | 40 | 0 |
| 1a(R)/iv/3 | 60 | 45 | 5 |
| 1a(S)/iv/3 | 65 | 40 | 0 |
| 1b(R)/iv/3 | 70 | 40 | 0 |
| 2a(R)/iv/3 | 65 | 55 | 10 |
| 2b(R)/iv/3 | 60 | 50 | 10 |
| 2a(S)/iv/3 | 60 | 55 | 10 |
| 3a(R)/iv/3 | 70 | 55 | 10 |
| 3b(S)/iv/3 | 65 | 50 | 5 |
| 3b(R)/iv/3 | 65 | 50 | 10 |
| 4a(R)/iv/3 | 60 | 35 | 0 |
| 4a(S)/iv/3 | 60 | 40 | 0 |
| 4b(R)/iv/3 | 60 | 35 | 0 |
| Saline controls)/i.v. 0,1 ml/100 g p.c. | (100% of animals) | (90% of animals) | (80% of animals) |
| 5a(R)/iv/3 | 70 | 50 | 20 |
| 5b(S)/iv/3 | 70 | 50 | 20 |
| 6a(R)/iv/3 | 65 | 45 | 5 |
| 6b(R)/iv/3 | 60 | 45 | 5 |
| 7a(R)/iv/3 | 40 | 20 | 0 |
| 7a(S)/iv/3 | 40 | 10 | 0 |
| 7b(R)/iv/3 | 50 | 30 | 0 |
| 7b(S)/iv/3 | 60 | 35 | 0 |
| 8a(S)/iv/3 | 45 | 20 | 0 |
| 9a(R)/iv/3 | 50 | 40 | 5 |
| 10a(R)/iv/3 | 60 | 50 | 10 |

(*): L-arginine methylester;
( ): D-arginine methylester;
(°): L-arginine ethylester.

IN VIVO ACTIVITY IN THE RAT (CEREBRAL ISCHEMIA)

The model described by Kramer (Kramer W., Tuynmann J. A.; Brain Research 6, 686 (1967)) has been used.

Two electrodes for the bipolar recording of EEG (occipito-cervical and cerebellar area) were applied to rats, anaesthetized with $N_2O$ (70%) and $O_2$ (30%), after i.v. tubocurarine treatment. Ischemia was induced by increasing the intracranial pressure in cisterna magna with artificial C.S.F. and for the duration of 1 minute. EEG was recorded 3' before ischemia, during the first 6 minutes of the recirculation and up to 30' after ischemia. The time for a complete EEG recovering was measured.

The compounds were administered i.v. 10' before test.

The results are reported in Table II.

TABLE II

| Compound/ dose mg/kg/i.v. | EEG recovery (time:seconds) |
|---|---|
| Controls (saline) | 73 ± 7 |
| L.A.M./3 | 61 ± 8 |
| D.A.M./3 | 45 ± 6 |
| 1a(S)/3 | 63 ± 6 |
| 4a(R)/3 | 58 ± 7 |
| 7a(R)/3 | 49 ± 6 |
| 7a(S)/3 | 43 ± 5 |

TABLE II-continued

| 10a(R)/3 | 62 ± 8 |
|---|---|

We claim:

1. A compound of formula I $$R_3-NH-\underset{\underset{R_2=N}{\|}}{C}-N(R_1)-A-\underset{\underset{NH_2}{|}}{C}(R_5)-COOR_4 \quad (I)$$

wherein
$R_1$ is hydrogen or methyl;
$R_2$ and $R_3$, which are the same or different, represent hydrogen or methyl, or taken together with the amidine system form an imidazole or imidazoline ring;
$R_4$ is a linear or branched $C_1$-$C_{10}$ alkyl group;
$R_5$ is hydrogen or methyl;
A is a chain of formula $-HN-CH_2-CH_2-$ or of formula $-N=CH-CH_2-$; a 1,4-cyclohexylene group optionally substituted by one or more methyl groups; or a 1,4-phenylene group optionally substituted by one or more halogen atoms, $C_1$-$C_4$ alkyl groups or $C_1$-$C_4$ alkoxy groups, a stereoisomer or a pharmaceutically acceptable salt thereof.

2. A compound according to claim 1, wherein A is a chain of formula $-NH-CH_2-CH_2$ or $-N=CH-CH_2-$.

3. A compound according to claim 1 wherein $R_1$, $R_2$, $R_3$ and $R_5$ are hydrogen, and A is a 1,4-cyclohexylene residue optionally substituted by one or more methyl groups.

4. A compound according to claim 1, wherein $R_1$, $R_2$, $R_3$ and $R_5$ are hydrogen, and A is 1,4-phenylene residue optionally substituted by one or more halogen atoms, $C_1$-$C_4$ alkyl groups or $C_1$-$C_4$ alkoxy groups.

5. A pharmaceutical composition having cytoprotective activity in ischemic or hypoxic conditions and cardioprotective activity containing as the principal active ingredient an effective amount of a compound according to any of claims 1–4 in admixture with a pharmaceutically acceptable carrier.

6. A pharmaceutical composition according to claim 5 in which the principal active ingredient is a compound according to claim 2.

7. A pharmaceutical composition according to claim 5 in which the principal active ingredient is a compound according to claim 3.

8. A pharmaceutical composition according to claim 5 in which the principal active ingredient is a compound according to claim 4.

9. A method for treating ischemic, hypoxic and cardiac conditions which comprises adminstering to a patient a composition according to claim 5 in admixture with a pharmaceutically acceptable carrier.

10. A method for treating ischemic, hypoxic and cardiac conditions which comprises administering to a patient a composition having cytoprotective activity containing as the principal active ingredient an effective amount of a member selected from the methyl and ethyl esters of arginine, a stereoisomer, or a pharmaceutically acceptable salt thereof, in admixture with a pharmaceutically acceptable carrier.

* * * * *